(12) United States Patent
Sugimoto et al.

(10) Patent No.: US 6,712,962 B2
(45) Date of Patent: Mar. 30, 2004

(54) ION CHROMATOGRAPHY SYSTEM FOR EXCHANGING AN ION EXCHANGER IN A SUPPRESSOR AND A SUPPRESSOR MEANS

(75) Inventors: Tadanori Sugimoto, Sagamihara (JP); Akiyoshi Miyanaga, Kawasaki (JP)

(73) Assignee: Tosoh Corporation, Tamaguchi-ken (JP)

( * ) Notice: Subject to any disclaimer, the term of this patent is extended or adjusted under 35 U.S.C. 154(b) by 0 days.

(21) Appl. No.: 09/918,498

(22) Filed: Aug. 1, 2001

(65) Prior Publication Data

US 2002/0014446 A1 Feb. 7, 2002

(30) Foreign Application Priority Data

Aug. 2, 2000 (JP) ........................................ 2000-238869

(51) Int. Cl.$^7$ ............................................... B01D 15/08
(52) U.S. Cl. ........................ 210/189; 210/198.2; 422/70
(58) Field of Search ........................... 210/189, 198.2, 210/267; 422/70

(56) References Cited

U.S. PATENT DOCUMENTS

| | | | | |
|---|---|---|---|---|
| 3,512,642 A | * | 5/1970 | Bevans | 210/189 |
| 4,455,233 A | * | 6/1984 | Pohl et al. | 210/198.2 |
| 4,808,317 A | * | 2/1989 | Berry et al. | 210/660 |
| 4,861,555 A | * | 8/1989 | Mowery | 422/70 |
| 5,567,307 A | * | 10/1996 | Karmarkar | 210/198.2 |
| 5,759,405 A | | 6/1998 | Anderson, Jr. et al. | 210/656 |
| 6,153,101 A | * | 11/2000 | Schafer et al. | 210/198.2 |

FOREIGN PATENT DOCUMENTS

| | | |
|---|---|---|
| EP | 0 605 826 A1 | 7/1994 |
| EP | 0 725 272 A1 | 8/1996 |

* cited by examiner

*Primary Examiner*—Ivars C. Cintins
(74) *Attorney, Agent, or Firm*—Sughrue Mion, PLLC

(57) ABSTRACT

An ion chromatography system having a suppressor means which is provided with a main body for accommodating an ion exchanger ready for measuring; a chamber for accommodating a virgin ion exchanger, and an automatic exchanging means which discharges a used ion exchanger from the main body after an optional number of times of measurement and supplies the ion exchanger accommodated in the chamber to the main body.

Figure 1:
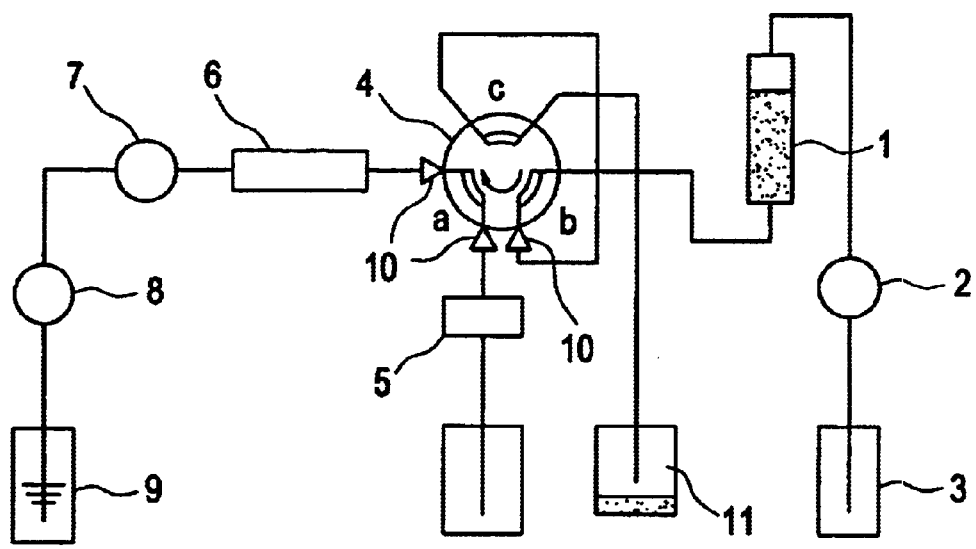

The ion chromatography system can measure a slight amount of ion species in a sample at a high sensitivity by conducting continuously a large number of times of measurement while the discharge of waste liquid can be minimized without causing a reduction of suppressing effect and a reduction of resolution performance of a desired ion species.

3 Claims, 2 Drawing Sheets

ION CHROMATOGRAPHY SYSTEM FOR EXCHANGING AN ION EXCHANGER IN A SUPPRESSOR AND A SUPPRESSOR MEANS

The present invention relates to an ion chromatography system comprising a suppressor means which is provided with an exchanging means for exchanging a used ion exchanger with a new ion exchanger every predetermined number of times of measurement, and an ion exchanging means for exchanging automatically a used ion exchanger with a new ion exchanger.

Ion chromatography (hereinbelow, referred to as IC) is a widely used technique to analyze cations or anions in a sample. In IC, an elute is used when such ion species is separated in a separating means such as a separating column. However, when the electric conductivity of the elute is high, a signal of slight amount originated from a desired ion species can not be detected even though an eluted liquid from the separating means is detected by an electric conductivity detector.

Therefore, there has conventionally been proposed such a technique that after a desired ion species has been separated by a separating means; ions in an eluted liquid are substituted by ions of a weak ion type by using means called a suppressor, and then the detection of the desired ion species is conducted.

There have been known suppressors as follows.

(1) A filler bed type suppressor (disclosed in JP-B-56-23100)

(2) A suppressor with an ion exchanging membrane (disclosed in JP-B-62-29024, JP-B-3-68344, JP-B-3-44670 and JP-B-5-48423)

(3) A suppressor for repeating the regeneration of the column (disclosed in JP-B-8-502830 and EP725272B1)

(4) A suppressor for regenerating electrochemically (disclosed in U.S. Pat. No. 5,633,171 and U.S. Pat. No. 5,759,405)

The filler bed type suppressor in (1) is a suppressor comprising a column filled with an ion exchange resin. This suppressor has a problem as follows. A time for analyzing (the number of times of measurements) is restricted inevitably owing to the capacity of the suppressor column since ion exchange groups on the ion exchange resin filled in the suppressor column are substituted by counter-ions in a desired ion species included in a sample or an eluted liquid. When a column having a sufficient capacity is used in order to overcome such disadvantage, there causes a reduction in the resolution ability of the desired ion species. In the determination of nitride, in fact, there has been known that a result of measurement varies remarkably due to the consumption of the suppressor column. In order to conduct the measurement continuously while a reduction in the resolution ability of the ion species is prevented, it is necessary to exchange the suppressor column or regenerate it. However, such exchange or regeneration can not be carried out unless the operation of the liquid transferring means is stopped to release a pressure applied to the flow passage system because the suppressor column is assembled in the flow passage of the chromatography system. Further, there is a problem that the measurement can not be re-opened unless non-abnormality in the flow passage system is confirmed after the exchange of the suppressor column, and unless an inner pressure of the flow passage system being the same as that in the previous measurement is confirmed. The above-mentioned problems are described in Japanese Patent No. 2750002 and JP-A-9-511838.

The membrane type suppressor in (2) is proposed to overcome the problems in the filler bed type suppressor. This suppressor is to obtain a stable suppressing effect even in a case of conducting continuous measurement. Specifically, ions in an eluted liquid are substituted by ions of a weak ion type while the eluted liquid and a regenerating liquid are passed by interposing therebetween an ion exchange membrane, whereby ion exchange groups on the ion exchange membrane, which are substituted by counter-ions of a desired ion species included in a sample or the eluted liquid, are regenerated. Although the membrane type suppressor is capable of conducting continuous measurement for a long time (a large number of times) which is difficult in the filer type suppressor, it is necessary to flow always and stably the regenerating liquid in order to regenerate stably ion exchange groups. Accordingly, a pump or a device of high accuracy is required. Further, there cause problems of environment and cost because a large amount of waste liquid is produced. In addition, since there is a limit in a mechanical strength of the ion exchange membrane, and when a back pressure in the suppressor increases due to any cause, the membrane is broken, whereby the regenerating liquid is mixed with the eluted liquid, with the result that the detection of a desired ion specie becomes impossible. Such problems are described in Japanese Patent No. 2750002 and JP-A-9-511838.

The suppressor for repeating the regeneration of the column in (3) has been proposed to overcome the problem in the filler bed type suppressor in (1). This suppressor has such flow passage system that at least two suppressor columns can selectively be used by using a flow passage switching device so that continuous measuring becomes possible. Specifically, while measurement is conducted by using one of the two suppressor columns, a regenerating liquid is supplied to the other suppressor column, whereby ions in an eluted liquid are substituted by ions of a weak ion type in the former suppressor column, and ion exchange groups on an ion exchange resin are regenerated in the other suppressor column. This suppressor permits continuous measurement for a long time (a large number of times) which was difficult in the filler bed type suppressor in (1), and a reduction in the resolution ability can be suppressed because the capacity per each suppressor column can be reduced. However, since this suppressor has to be operated by switching, in fact, two or three suppressor columns, suppressor requires a pump or a device which passes always the regenerating liquid in a stable manner, to regenerate the suppressor columns in a short time. Further, there cause problems of environment and cost because a large amount of waste liquid is produced. In addition, there is a problem that the ion exchange resin filled in the suppressor columns is stained by a certain kind of heavy metal or organic material during a repetitive use for a long term, whereby a regenerating liquid used usually (e.g., 20 mmol/l of $H_2SO_4$ and NaOH) can not provide a sufficient regeneration, and a suppressing performance is reduced.

The suppressor for regenerating electrochemically in (4) is such that an eluted liquid from one suppressor column is introduced into the other suppressor column, and then, the eluted liquid from the later is regenerated by electrolysis. In this suppressor, however, there is a problem that due to a limitation by the relation between the area of electrodes and an applied voltage, an inner shape of the suppressor causes a reduction in the resolution ability of to a desired ion species.

It is an object of the present invention to provide an ion chromatography system capable of conducting continuously a large number of times of measurement to measure with a high sensitivity a slight amount of ion species in a sample without the necessity of passing continuously the regenerating liquid, hence, minimizing the discharge of waste liquid, and without causing a reduction in the suppressing effect or a reduction in the resolution ability of a desired ion species.

It is an object of the present invention to provide an ion exchanging means for exchanging automatically a used ion exchanger with a new ion exchanger.

In accordance with an aspect of the present invention, there is provided an ion chromatography system wherein a desired ion species in a sample is separated by a separating means; an eluted liquid from the separating means is introduced into a suppressor means, in which an ion exchanger is held, to reduce the electric conductivity of the eluted liquid, and the eluted liquid from the suppressor is introduced into a detector to detect desired ions, the ion chromatography system being characterized in that the suppressor means is provided with a main body for accommodating an ion exchanger ready for measuring; a chamber for accommodating a virgin ion exchanger, and an automatic exchanging means which discharges a used ion exchanger from the main body after an optional number of times of measurements and supplies the ion exchanger accommodated in the chamber to the main body.

According to the present invention, there is provided the ion chromatography system according to the first aspect wherein the suppressor means comprises a 6-way switching rotary valve having 3 rotary grooves a, b and c, a chamber for accommodating a virgin ion exchanger in a slurry state, a liquid transferring tank which accommodates a transferring liquid for introducing the ion exchanger in a slurry state in the chamber into the rotary valve, and a liquid transferring means for supplying the transferring liquid; a flow passage from the separating means is connected to a flow passage to the detector by means of the rotary groove a; a flow passage from the liquid transferring means to the chamber is connected to a flow passage to a third rotary groove by means of the rotary groove b; a flow passage from the rotary groove b is connected to a flow passage to the outside of the main body by means of the rotary groove c, and each filter which prevents the ion exchanger from passing through is provided at a side of the separating means with respect to the rotary groove a, at a side of the detecting means with respect to the rotary groove a and at a side of the rotary groove c with respect to the rotary groove b.

According to the present invention, there is provided the ion chromatograph system according to the first aspect wherein the suppressor means comprises a tube having both ends which are tightly closed with sealing materials capable of passing only a string-like ion exchanger; a chamber for accommodating a virgin string-like ion exchanger, and a supply means which introduces the string-like ion exchanger in the chamber into the tube from its one end and discharges it from the other end of the tube; a portion in the vicinity of one end of the tube is connected to a flow passage from the separating means, and a portion in the vicinity of the other end of the tube is connected to the detecting means.

According to the present invention, there is provided the ion chromatography system according to the first aspect wherein the exchanging means is to replace the used ion exchanger by a new ion exchanger every predetermined number of times of measurement.

According to the present invention, there is provided the ion chromatography system according to the first aspect wherein the ion exchanger is an ion exchange resin or ion exchange fibers.

In accordance with a second aspect of the present invention, there is provided an ion exchanging means for holding an ion exchanger which comprises a holding section for accommodating an ion exchanger ready for measuring, a chamber for accommodating a virgin ion exchanger, and an automatic exchanging means which discharges a used ion exchanger from the main body after an optional number of times of measurements and supplies the ion exchanger accommodated in the chamber to the main body.

According to the present invention, there is provided the ion exchanging means according to the second aspect, wherein the ion exchanging means comprises a 6-way switching rotary valve having 3 rotary grooves a, b and c, a chamber for accommodating a virgin ion exchanger in a slurry state, a liquid transferring tank which accommodates a transferring liquid for introducing the ion exchanger in a slurry state in the chamber into the rotary valve, and a liquid transferring means for supplying the transferring liquid.

According to the present invention, there is provided the ion exchanging means according to the second aspect, wherein the ion exchanging means comprises a tube having both ends which are tightly closed with sealing materials capable of passing only a string-like ion exchanger; a chamber for accommodating a virgin string-like ion exchanger, and a supply means which introduces the string-like ion exchanger in the chamber into the tube from its one end and discharges it from the other end of the tube.

According to the present invention, there is provided the ion exchanging means according to the second aspect, wherein the exchanging means is to replace the used ion exchanger by a new ion exchanger every predetermined number of times of measurement.

According to the present invention, there is provided the ion exchanging means according to the second aspect, wherein the ion exchanger is an ion exchange resin or ion exchange fibers.

Figure 2:
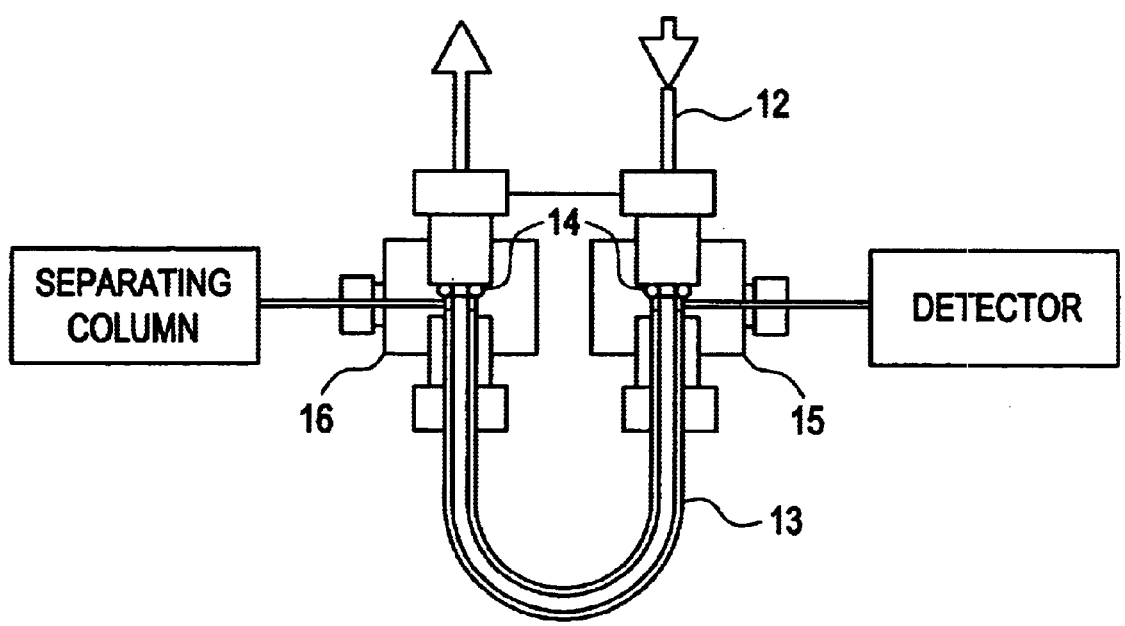
Figure 3:
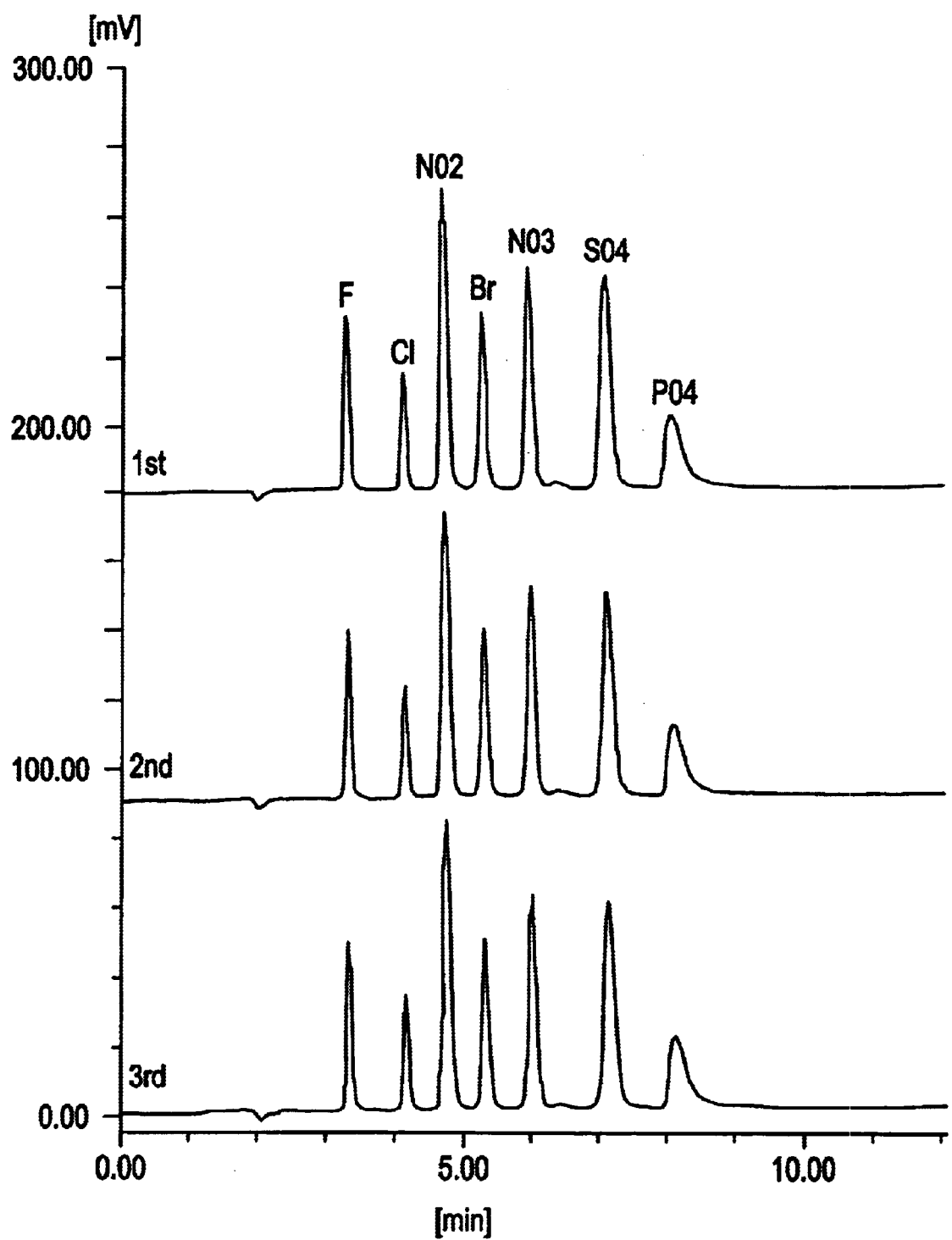

In drawings:

FIG. 1 is a diagram showing an embodiment of the suppressor means and the IC system with such suppressor means of the present invention;

FIG. 2 is a diagram showing an embodiment of the suppressor means and the IC system with such suppressor means of the present invention; and FIG. 3 is a diagram showing a result of measurement of anions as standard in the IC system shown in FIG. 1. In FIG. 3, a result of measurement in the first time (1st), a result of measurement in the second time (2nd) and a result of measurement in the third time (3rd) are shown sequentially from an upper portion wherein the abscissa represents an eluation time (min) of each desired ion species, and the ordinate represents an arbitrary unit. Further, in FIG. 3, F represents fluoride ion, Cl chloride ion, $NO_2$ nitrous acid ion, Br bromide ion, $NO_3$ nitric acid ion, $SO_4$ sulfuric acid ion, and $PO_4$ phosphoric acid ion respectively.

In the following, the present invention will be described in detail.

In order to solve the above-mentioned problems, the present invention adopts such construction that an ion exchanger required for an optional number of times of measurement is accommodated in a main body; the ion exchanger is discharged from the main body when the optional number of times of measurement is finished, and a virgin ion exchanger is automatically supplied to the main body. Namely, only a small amount of ion exchanger, which is required for an optional number of times of measurement, is used, and after the optional number of times of measurement, a used ion exchanger is discharged from the main body to exchange it with a virgin ion exchanger so that the main body exchanged with the virgin ion exchanger can be used repeatedly. Accordingly, a correct analysis of a desired ion species can always be realized without causing a reduction in the resolution ability and minimizing the consumption of the ion exchanger. It is needless to say that the used ion exchanger, after being discharged from the main body, can be regenerated, regardless of the measurement, i.e., in a location isolated from the flow passage system for the measurement, and then, the regenerated ion exchanger is usable again as a virgin ion exchanger. By conducting the regeneration regardless of the measurement, there is no limitation to a time for regeneration, and the regeneration can be conducted in a sufficient time. Accordingly, in the present invention, it is unnecessary to consume and waste a large amount of regenerating liquid as in the conventional technique.

The suppressor means in the IC system of the present invention accommodates an ion exchanger in a volume capable of performing a sufficient suppressing effect for an optional number of times of measurement in the main body. The ion exchanger may be an ion exchange resin, ion exchange fibers, an ion exchange membrane or the like, which is selected suitably depending on a desired ion species to be suppressed. The volume of such ion exchanger, which is sufficient for an optional number of times of measurement may be determined by, for example, conducting preparatory tests. Besides the ion exchanger accommodated in the main body, a virgin ion exchanger is accommodated in the chamber. Then, a used ion exchanger in the main body, which has been used for an optional number of times of measurement, is discharged from the main body by means of the automatic exchanging means, and at the same time or thereafter, a virgin ion exchanger is supplied automatically from the chamber to the main body by means of the automatic exchanging means.

The IC system of the present invention may be so constructed that after the completion of an optional number of times of measurement, an operator of the IC system exchanges the used ion exchanger with a virgin one by operating the automatic exchanging means. However, it is preferable to provide such construction that for example, a control means is provided in the IC system to exchange automatically the ion exchanger without any instruction from an operator when an optional number of times of measurement is finished.

The optional number of times is preferably 1 to 5 times. It is because the volume of the ion exchanger required for 1 to 5 times of measurement is very small, and accordingly, it is advantageous to reduce the size of the ion exchanging means including the main body, and it is in particular preferable to increase reliability on the IC system and obtaining a highly accurate result of measurement.

Each means other than the suppressor means in the IC system according to the present invention is the same as that in conventional IC systems described in this specification as the conventional techniques. As an example, there are a sample transferring means for transferring automatically a sample to be measured to a predetermined position in a sampling means (an automatic sampler), the sampling means for sampling automatically a predetermined quantity of sample, a liquid transferring pump for transferring the predetermined quantity of sample to a separating means, the separating means such as a separating column filled with an ion exchange resin, in which a desired ion species is separated from the transferred sample, an elute optimized to separate the desired ion species in the separating column, the suppressor means used in the present invention, a detecting means such as an electric conductivity detector for detecting the desired ion species, means for observing an electric signal from the detecting means or outputting the electric signal on a chart, and for storing the electric signal as electronic data, a liquid transferring means, a sampling means, a control means for controlling the detecting means and so on, and a connecting means such as a pipe, a cable or the like which connects the above-mentioned means to send and receive the liquid and the electric signal. It is possible to add any means other than the above-mentioned or to remove an unnecessary means depending on circumstances.

The suppressor means in the above-mentioned IC system can be used solely as an ion exchanging means (it is natural to achieve an ion exchanging performance to an ion species providing a suppressing effect in a case of being used as a suppressor means).

In the following, description will be made in more detail on the suppressor means and the IC system with the suppressor means according to the present invention with reference to the drawings. However, the embodiments shown in the drawings are merely examples of the present invention, and the present invention is not limited thereto.

FIG. 1 shows a concrete example of an ion exchanging means and a IC system provided with the ion exchanging means as a suppressor means according to the present invention. In FIG. 1, reference numeral 1 designates a chamber accommodating a virgin ion exchanger (an ion exchange resin in a slurry state), numeral 2 designates a liquid transferring means (a liquid transferring pump) for transferring the virgin ion exchanger to a main body of suppressor means, numeral 3 designates a liquid transferring tank accommodating a transferring liquid for transferring the virgin ion exchanger to the main body of suppressor means (the transferring liquid does not influence the measurement of a desired ion species), numeral 4 designates the main body of suppressor means which utilizes a 6-way switching rotary valve provided with three rotary grooves a, b and c, numeral 5 designates a detecting means (an electric conductivity detector), numeral 6 designates a separating means filled with an ion exchange resin to separate a desired ion species (an ion exchange column), numeral 7 designates a sampler for sampling a predetermined quantity of sample, numeral 8 designates a liquid transferring pump, numeral 9 designates a tank for an elute, numeral 10 designates a filter which permits the transferring liquid to pass through, but does not allow the ion exchanger to pass through, and numeral 11 designates a tank receiving a discharged used ion exchanger.

In the suppressor means, a flow passage from the separating means is connected to a flow passage to the detecting means by means of the rotary groove a; a flow passage from the liquid transferring means to the chamber is connected to a flow passage to a third rotary groove by means of the rotary groove b; a flow passage from the rotary groove b is connected to a flow passage to the outside of the main body by means of the rotary groove c, and each filter 10 which prevents the ion exchanger from passing through is provided at a side of the separating means with respect to the rotary groove a, at a side of the detecting means with respect to the rotary groove a and at a side of the rotary groove c with respect to the rotary groove b.

In the example shown in FIG. 1, the ion exchanger used for measuring is held at the position of the groove a of the rotary valve; a virgin ion exchanger is introduced automatically to the position of the groove b, and a used ion exchanger is discharged automatically outside of the main body from the position of the groove c. Accordingly, the rotary valve constitutes the main body of suppressor means and a part of an automatically exchanging means which discharges automatically the used ion exchanger outside of the main body and introduces automatically a new ion exchanger from the chamber.

In the construction of this example that an ion exchange resin is used as an ion exchanger, and the ion exchanger is transferred from the chamber to the main body of suppressor means every predetermined number of times of measurement, it is preferable to use the ion exchanger in a form of fine particles of from 10 $\mu$m to 500 $\mu$m. In case that the particle diameter is extremely smaller than 10 $\mu$m, the ion exchanger precipitates and solidifies at the bottom of the chamber even though it is in a slurry state, whereby it may be difficult to transfer it to the suppressor main body. Therefore, it is necessary to dispose a stirring means in the chamber or at a suitable location. Further, it is necessary to reduce the size of openings of the filter disposed in the suppressor means, which is to transfer a predetermined quantity of ion exchanger to the suppressor means, or it is necessary to cope with a problem such as a pressure increase in a transferring passage for the ion exchanger. In the structure of this example, on the contrary, when the particle diameter is extremely larger than 500 $\mu$m, the packing density in a case of transferring and filling the ion exchanger in the suppressor main body becomes low.

In FIG. 1, suppression is carried out, at the groove a of the rotary valve, to an eluted liquid from the separating means 6, and the eluted liquid after the suppression is detected by the detecting means 5. At this moment, the ion exchanger accommodated in a slurry state in the chamber 1 is transferred to the groove b in a state that the ion exchanger is dispersed in the transferring liquid, and is charged in the groove b by means of the liquid transferring means 2. A filter 10 which prevents the ion exchanger from passing through is attached to the outlet at the side of the groove c of the groove b. Accordingly, after a predetermined quantity of ion exchanger has been charged in the groove c, only the transferring liquid is transferred, whereby there is no possibility of consuming the ion exchanger beyond a predetermined quantity even when the liquid transferring means 2 is operated continuously. In the continuous liquid transferring operation by the liquid transferring means 2, the transferring liquid is passed through the groove b and then, is discharged. In this case, the discharged transferring liquid is introduced into the groove c to discharge the used ion exchanger in the groove c to the tank 11. The tank can be replaced by another empty tank optionally so that the used ion exchanger is regenerated. In the present invention, since it is unnecessary to conduct the regeneration within a predetermined time, after the completion of all the measurements for instance, the liquid in the tank may be substituted with a regenerating liquid for regenerating the ion exchanger, the substituted liquid being left for a while.

When a measurement is finished, for example, the rotary valve 4 as the main body is rotated clockwise 120° so that the groove located at the position of the groove b is moved to the position of the groove a in FIG. 1. Then, the next measurement is conducted to repeat the before-mentioned process in such condition.

In the above-mentioned example, the 6-way rotary valve having three rotary grooves is used. However, use of the 6-way valve is not always be essential. For example, the function of the present invention that the ion exchanger is introduced automatically can be achieved even by combining a 4-way rotary valve having two rotary grooves with an electromagnetic valve, or combining two sets of the 4-way rotary valve.

FIG. 2 is a diagram showing a concrete example of the ion exchanging means of the present invention and an IC system provided with the ion exchanging means as a suppressor means. In FIG. 2, reference numeral 12 designates a string-like ion exchanger (ion exchange fibers) (in this example, a portion of ion exchange fiber inserted in a tube functions as an ion exchanger used for measuring), numeral 13 designates a U-like tube and numeral 14 designates a sealing material (an O-ring) provided at each end of the U-like tube to allow only the string-like ion exchanger 12 to pass through. In FIG. 2, a supply means (comprising a motor and a winding tool) which inserts the ion exchanger from an end of the U-like tube to the inside of the tube in a direction of arrow mark and discharges the ion exchanger outside of the tube through the other end in a direction of arrow mark and a chamber accommodating a virgin ion exchanger are not shown.

In this example, an end of the U-like tube is connected to a flow passage from the separating means by means of a joint 16, and the other end of the U-like tube is connected to a flow passage to the detecting means by means of a joint 15, whereby the eluted liquid introduced into the U-like tube through the joint 16 is brought to contact with the ion exchanger for the suppression, and is introduced into the detecting means through the joint 15 where the detection is conducted.

In this example of FIG. 2, the U-like tube is the main body of suppressor; a portion (not shown) accommodating the ion exchanger which is before being introduced into the U-like tube is the chamber, and the before-mentioned supply means is the automatic exchanging means.

As in this example, in the structure that ion exchange fibers are used as the ion exchanger in the suppressor means, and the ion exchanger is discharged from the U-like tube as the main body of suppressor means every predetermined number of times of measurement, ion exchange fibers having a predetermined length, elasticity and a tensile strength, a supply means comprising a motor for supplying the ion exchange fibers by winding, and sealing materials which permit to introduce the ion exchange fibers into the U-like tube and to discharge them from the tube, while preventing an eluted liquid flowing in the U-like tube from leaking the outside, are required. The ion exchange fibers may be a commercially available product, and each of the sealing materials is preferably a silicon sealing material or the like which is inactive to the eluted liquid and is excellent in hard wearing.

EXAMPLE

In the IC system of the present invention shown in FIG. 1, a mixed aqueous solution of 1.2 mM of sodium tetraborate, 0.2 mM of sodium carbonate and 6.5 mM of sodium hydroxide as the elute; TSKgel Super IC-Anion (tradename, manufactured by TOSOH CORPORATION; inner diameter: 4.6 mm, length: 15 cm) as the separating column; Muromac 50 W×8 (tradename, manufactured by Muromachi Kagaku Kabushiki Kaisha) as the ion exchanger, and pure water as the transferring liquid for the ion exchanger, were used, and anions as standard (a mixed aqueous solution of 1 fluoride ion 2 mg/l, 2 chloride ion 2 mg/l, 3 nitrous acid ion 10 mg/l, 4 bromide ion 10 mg/l, 5 nitric acid ion 10 mg/l, 6 sulfuric acid ion 10 mg/l, 7 phosphoric acid ion 20 mg/l) were measured continuously for each 20 $\mu$l three times under conditions of a flow rate of 0.8 ml/min and a column temperature of 40° C. FIG. 3 shows a chromatograph as a result of measurement.

The volume of each of the grooves a, b and c of the suppressor means 4 was 200 μl. In this Example, the rotary valve as the main body of the suppressor means was rotated to exchange the ion exchanger for each time of measurement. It became clear from FIG. 3 that a good suppressing effect could be achieved as a background electric conductivity of 7 μS/cm in each measurement, and a predetermined quantity of ion exchanger could correctly be exchanged with a new one for each measurement in the suppressor means in this Example and the IC system provided with such suppressor means, with the result that an excellent measurement of anions could be realized. The background electric conductivity of the eluted liquid in a case without using the suppressor was 1,200 μS/cm.

According to the present invention, the following effects are obtainable in comparison with the conventional suppressor means and the conventional IC system provided with such suppressor means.

(1) A sufficient amount of ion exchanger for exchanging can be prepared, and such ion exchanger is exchanged with a used ion exchanger, whereby ion exchange groups in the ion exchanger are substituted by counter-ions in a desired ion species containing in a sample or an eluted solution without causing reduction in the suppressing effect. Accordingly, there is no limitation to the number of times of measurement. Further, since a fresh ion exchanger can always be used, continuous measurement is possible without reducing correctness of measurement.

(2) Since continuous measurement can be conducted without increasing the capacity of the column, there is no possibility of causing reduction in the resolution ability.

(3) Even in a case of regenerating a used ion exchanger, it is unnecessary to finish the regeneration within a predetermined time. Accordingly, it is unnecessary to conduct the regeneration by supplying usually a regenerating liquid, whereby the consumption of a large amount of regenerating liquid can be prevented, and therefore, the production of a waste liquid can be prevented.

(4) Further, when a used ion exchanger is to be regenerated, the regeneration is possible in a place without influencing the flow passage system in IC. Accordingly, it is unnecessary to stop the operation of the liquid transferring means in IC to release a pressure applied to the flow passage system, and to confirm that there is no abnormality in the flow passage system after the regeneration and that an inner pressure and so on in the flow passage system is equal to that in the previous measurement.

(5) It is possible to prevent the deterioration of the ion exchanger due to the adsorption of an organic compound or a certain kind of heavy metal, as observed in the suppressor means for switching the suppressor column.

(6) As described in the concrete example, the suppressor means of the present invention can be constructed by using a rotary valve or the like, and a special device is not required. Accordingly, it is advantageous in cost.

(7) Since the suppression is conducted by merely supplying the elute, there is no reduction in the resolution ability of a desired ion species by an inner shape of the suppressor, which is determined by the relation between the area of electrodes and an applied voltage, in comparison with the suppression using an electrochemically controlling or an electrochemically regenerating technique.

What is claimed is:

1. An ion chromatography system comprising:
    a separating mechanism;
    a suppressor mechanism coupled to the separating mechanism, the suppressor mechanism adapted to receive an eluted liquid from the separating mechanism, the suppressor mechanism having a main body in which an ion exchanger is provided to reduce the electric conductivity of the eluted liquid from the separating mechanism; and
    a detector coupled to the suppressor mechanism to detect desired ions in the eluted liquid from the suppressor mechanism,
    wherein the suppressor mechanism includes automatic exchanging means for discharging the ion exchanger from the main body and for supplying a virgin ion exchanger to the main body,
    wherein the main body of the suppressor mechanism is a 6-way switching rotary valve having a first rotary groove a, a second rotary groove b and a third rotary groove c,
    wherein the suppressor mechanism includes a chamber, for accommodating a virgin ion exchanger in a slurry state, coupled to the rotary valve,
    wherein the automatic exchanging means includes (1) a liquid transferring tank, which accommodates a transferring liquid for introducing the virgin ion exchanger in a slurry state in the chamber into the rotary valve, and (2) a liquid transferring means for supplying the transferring liquid,
    wherein a flow passage from the separating mechanism is connected to a flow passage to the detector by the rotary groove a,
    wherein a flow passage from the liquid transferring means to the chamber is connected to a flow passage to the third rotary groove c by the second rotary groove b,
    wherein a flow passage from the second rotary groove b is connected to a flow passage to a discharge passage leading to the outside of the rotary valve by the third rotary groove c, and
    wherein filters, which prevent the passage of ion exchanger are respectively provided at (1) a side of the separating mechanism with respect to the first rotary groove a, (2) a side of the detector with respect to the first rotary groove a, and (3) a side of the third rotary groove c with respect to the second rotary groove b.

2. The ion chromatography system according to claim 1, wherein the automatic exchanging means replaces the ion exchanger in the main body with the virgin ion exchanger every time a predetermined number of detections are performed by the detector.

3. An ion chromatography system comprising:
    a separating mechanism;
    a suppressor mechanism coupled to the separating mechanism, the suppressor mechanism adapted to receive an eluted liquid from the separating mechanism, the suppressor mechanism having a main body in which an ion exchanger is provided to reduce the electric conductivity of the eluted liquid from the separating mechanism; and
    a detector coupled to the suppressor mechanism to detect desired ions in the eluted liquid from the suppressor mechanism,
    wherein the suppressor mechanism includes automatic exchanging means for discharging the ion exchanger from the main body and for supplying a virgin ion exchanger to the main body, wherein the main body of the suppressor mechanism is a tube having a first end and a second end, the first and the second ends being provided with sealing materials through which only a string-like ion exchanger is passable, wherein the suppressor mechanism includes a chamber, for accommodating a virgin string-like ion exchanger, coupled to the first end of the tube, wherein the automatic exchanging means includes supply means for introducing the string-like ion exchanger in the chamber into the tube from the first end and discharging the string-like ion exchanger from the second end, and wherein an input portion of the tube, which is located adjacent to the second end of the tube, is connected to a flow passage from the separating mechanism, and wherein an output portion of the tube, which is located adjacent to the first end of the tube, is connected to the detector.

* * * * *